United States Patent [19]

Wakao et al.

[11] Patent Number: 5,959,147
[45] Date of Patent: Sep. 28, 1999

[54] ORGANIC SULFIDE COMPOUND AND METHOD FOR PRODUCTION THEREOF

[75] Inventors: Norihiro Wakao; Youichi Hino; Ryuichi Ishikawa, all of Osaka, Japan

[73] Assignee: Nippon Shokubai Co., Ltd., Osaka-fu, Japan

[21] Appl. No.: 08/911,443

[22] Filed: Aug. 12, 1997

Related U.S. Application Data

[63] Continuation of application No. 08/745,009, Nov. 7, 1996, abandoned.

[51] Int. Cl.$^6$ ........................ C07C 235/08; C07C 321/14
[52] U.S. Cl. ............................ 564/201; 564/215; 564/500
[58] Field of Search ..................................... 564/201, 202, 564/215.5

[56] References Cited

U.S. PATENT DOCUMENTS 5,446,201  8/1995  Angenendt et al. ..................... 564/500

OTHER PUBLICATIONS

Hurd et al, J.Am. Chem. Soc., vol 69, pp 2328–2335, 1947.

*Primary Examiner*—Shailendra Kumar
*Attorney, Agent, or Firm*—Omri M. Behr, Esq.

[57] ABSTRACT

This invention concerns a novel organic sulfide compound obtained by the reaction of a mercapto alkanol such as 2-mercapto ethanol with an unsaturated amide such as (meth)acrylamide, maleic acid diamide, or fumaric acid diamide and a method for the production of the organic sulfide compound. The invention enables novel organic sulfide compounds of great commercial utility to be obtained with a high yield on a commercial scale.

6 Claims, 2 Drawing Sheets

ORGANIC SULFIDE COMPOUND AND METHOD FOR PRODUCTION THEREOF

This application is a continuation of application Ser. No. 08/745,009, filed Nov. 7, 1996, now abandoned.

BACKGROUND OF THE INVENTION

1. Field of the Invention

This invention relates to a novel organic sulfide amide compound and a method for the production thereof. The organic sulfide compounds are useful compounds as raw materials for the production of metal surface detergents, antioxidants for polymers, and various products of chemical industry.

2. Description of the Prior Art

The method for obtaining 3-[(2-hydroxyethyl)thio] propionitrile, the nitrile of a sulfur compound, by the reaction of acrylonitrile with 2-mercapto ethanol is reported only in J. Am. Chem. Soc., Vol. 69 (1947), page 2331 and the method for obtaining methyl 3-[(2-hydroxyethyl) thio] propionate, the ester of a sulfur compound, by the reaction of methyl acrylate with 2-mercapto ethanol is reported barely in J. Am. Chem. Soc., Vol. 69 (1947), page 2333.

The organic sulfide compounds according to this invention, however, have never occurred in the literature and are novel compounds.

An object of this invention, therefore, is to provide a novel organic sulfide compound.

Another object of this invention is to provide a method for producing a novel sulfide compound of great commercial utility with a high yield.

SUMMARY OF THE INVENTION

The objects mentioned above are accomplished by an organic sulfide compound represented by the general formula (I):

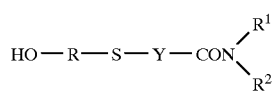
(I)

wherein R represents a hydrocarbon residue of 2 to 8 carbon atoms, $R^1$ and $R^2$ independently represent a hydrogen atom or a hydrocarbon residue of 1 to 4 carbon atoms, and Y represents a group of the formula (II):

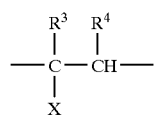
(II)

or of the formula (III):

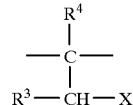
(III)

wherein $R^3$ and $R^4$ independently represent a hydrogen atom, methyl or ethyl and X represents a hydrogen atom or

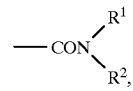

The objects mentioned above are further accomplished by a method for the production of an organic sulfide compound represented by the general formula (I):

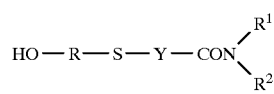
(I)

[wherein R represented a hydrocarbon residue of 2 to 8 carbon atoms, $R^1$ and $R^2$ independently represent a hydrogen atom or a hydrocarbon residue of 1 to 4 carbons atoms, and Y represents a group represented by the general formula (II):

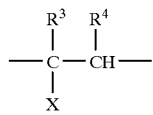
(II)

or of the formula (III):

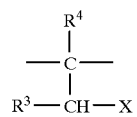
(III)

wherein $R^3$ and $R^4$ independently represent a hydrogen atom, methyl or ethyl and X represents a hydrogen atom or

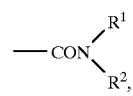

which method comprises" preacting a mercapto alkanol represented by the general formula (IV):

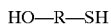   (IV)

(wherein R is as defined above) with an unsaturated amide represented by the general formula (V):

(wherein $R^1$ and $R^2$ are as defined above, $R^3$ and $R^4$ independently represent a hydrogen atom, a methyl group or an ethyl group, and X is as defined above).

The organic sulfide compounds of this invention are usable in various applications such as, for example, raw materials for the production of metal surface detergents, antioxidants for polymers, and various products of chemical industry. The compounds represented by the general formula (VI) which will be described specifically hereinbelow are particularly useful for such applications as mentioned above. Then, the method of this invention enables the novel organic sulfide compounds of great commercial utility represented by the aforementioned general formula (I) to be obtained with a high yield on a commercial scale by causing a mercapto alkanol represented by the general formula (IV) mentioned above to react with an unsaturated amide represented by the general formula (V) mentioned above.

DESCRIPTION OF THE PREFERRED EMBODIMENT

Figure 1:
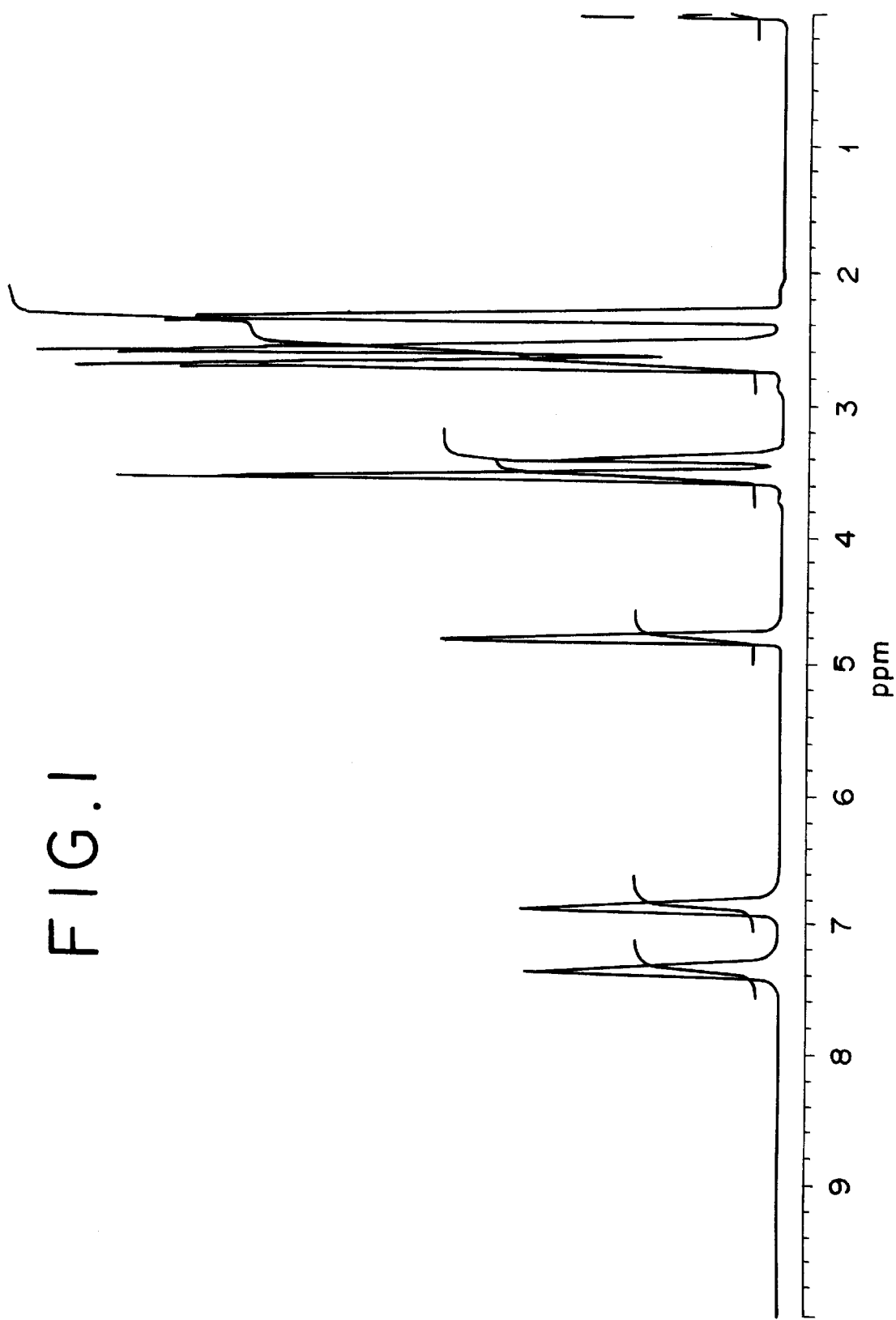
FIG. 1 is a nuclear magnetic resonance spectrum of $^1H$ of the 3-[(2-hydroxyethyl)thio]propion amide obtained in Example 1 of this invention in bidimethyl sulfoxide solvent according to the TMS standard.

The organic sulfide compounds according to this invention are compounds which are represented by the general formula (I) mentioned above. In this general formula (I), R represents a divalent hydrocarbon residue of 2 to 8, preferably 2 to 6, carbon atoms such as, for example, alkylene groups including ethylene, propylene, trimethylene, butylene, and 1,6-cyclohexylene. $R^1$ and $R^2$ independently represent a hydrogen atom or a hydrocarbon residue of 1 to 4, preferably 1 to 3, carbon atoms such as, for example methyl, ethyl, propyl, and butyl. Y represents a group represented by the general formula (II):

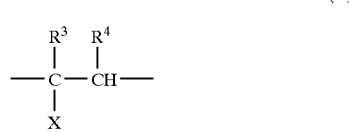

(wherein $R^1$ and $R^2$ are as defined above and X represents a hydrogen atom, or

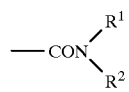

(wherein $R^1$ and $R^2$ are as defined above)) or the general formula (III):

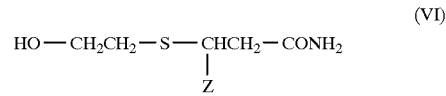

(wherein $R^1$, $R^2$, and X are as defined above).

Among these organic sulfide compounds, the compounds which are represented by the general formula (VI):

$$HO-CH_2CH_2-S-\underset{Z}{CHCH_2}-CONH_2 \qquad (VI)$$

(wherein Z represents a hydrogen atom or -CONH$_2$) are particularly useful because they are produced from readily available raw materials and they possess a great capability as a metal surface detergent.

The organic sulfide compounds of this invention include the following compounds, for example:

3-[(2-Hydroxyethyl)thio]propion amide; and
3-[(2-hydroxyethyl)thio]-3-carbamoyl-propion amide.

According to this invention, an organic sulfide compound represented by the general formula (I) is produced by the reaction of a mercapto alkanol represented by the general formula (IV) with an unsaturated amide represented by the general formula (V).

As concrete examples of the mercapto alkanol represented by the general formula (IV) to be used as a raw material, 2-mercapto ethanol, 1-mercapto ethanol, 3-mercapto propanol, 1-methyl-2-mercapto ethanol, 2-methyl-2-mercapto ethanol, 1,2-dimethyl-2-mercapto ethanol, 1-butyl-2-mercapto ethanol, and 1-cyclohexyl-2-mercapto ethanol may be cited.

As concrete examples of the unsaturated amide represented by the general formula (V) to be used as a raw material, acrylamide, methacrylamide, 2-ethyl-acrylamide, maleic acid diamide, fumaric acid diamide, and 1-methyl-maleic acid diamide may be cited.

According to the method of this invention, the novel organic sulfide compounds represented by the general formula (I) are obtained from such raw materials as mentioned above. When 3-[(2-hydroxyethyl)thio]propion amide and/or 3-[(2-hydroxyethyl)thio]-3-carbamoyl-propion amide are to be produced by using 2-mercapto ethanol as the mercapto alkanol and acrylamide, maleic acid diamide, and/or fumaric acid diamide as the unsaturated amide, the raw materials are readily available and the products are obtained with a high yield on a commercial scale.

The amount of the mercapto alkanol to be used in the present invention is in the range of 0.5 to 3 mols, preferably 0.8 to 1.5 mols, based on 1 mol of the unsaturated amide. When the mercapto alkanol is used in an excess amount relative to that of the unsaturated amide, the unsaturated amide is quickly converted to the organic sulfide compound aimed at and the amount of the residual unsaturated amide is enabled to decrease. If it is used in an amount exceeding 3 mols, however, the disadvantage arises that the effects mentioned above will be scarce and the amounts of unaltered mercapto alkanol to be recovered after the reaction will be unduly large. Conversely, if the amount of the mercapto alkanol to be used is less than 0.5 mol per mol of the unsaturated amide, the disadvantage likewise ensues that the amount of the unaltered unsaturated amide will increase and, as a result, the unsaturated amide will undergo such secondary reactions as polymerization and the unaltered unsaturated amide to be recovered after the reaction will grow in amount.

In this invention, for the purpose of curbing the polymerization, the reaction mixture prepared for the production may incorporate therein a polymerization inhibitor such as, for example, a benzoquinone derivative or a nitro compound.

In this invention, the reaction may be carried out without using a solvent. Since this reaction is exothermic in nature, the reaction system must be deprived of heat during the course of the reaction. For the purpose of exalting the efficiency of the removal of heat, the reaction may allow the use of a solvent as a diluent. This solvent is only required to be inactive to the reaction and is not limited in any other respect. As concrete examples of the solvent, various solvents such as saturated aliphatic hydrocarbons such as pentane, hexane, and cyclohexane, aromatic hydrocarbons such as benzene, toluene, and xylene, polar non-protonic compounds such as acetone, dimethyl sulfoxide, dimethyl formamide, and N-methyl pyrrolidone, halogenated alkyls such as methylene chloride and chloroform, ethers such as dioxane, ethylene glycol dimethyl ether and tetrahydrofuran, alcohols such as methanol, ethanol, n-propanol, and isopropanol, and water maybe cited. These solvents may be used either singly or in the form of a mixture of two or more members. Particularly, water has many advantages such as curbing polymerization of unsaturated amides, promoting the reaction aimed at, permitting highly efficient removal of heat, and being inexpensive and non-toxic. It is, therefore, highly appropriate to use water as the solvent herein from the commercial point of view.

The reaction temperature is selected appropriately and not critically in the range of 20° to 150° C. If the reaction temperature is less than 20° C., the reaction velocity will be lowered and the reaction time will be elongated to the extent of impairing the economy of the reaction. Conversely, if it exceeds 150° C., the disadvantage arises that the reaction will entrain such secondary reactions as polymerization of unsaturated amides and the yield of the reaction will be consequently lowered.

In this invention, the reaction may be carried out without using a catalyst. For the purpose of exalting the reaction velocity, it can be carried out in the presence of a solid basic catalyst such as, for example, an anion-exchange resin. The anion-exchange resins which are effectively usable as the catalyst herein include various types of anion-exchange resins which have tertiary amines or quaternary ammonium hydroxides as functional groups, for example.

The amount of the catalyst to be used is in the range of 0.5 to 40% by weight, preferably 1 to 20% by weight, based on the amount of the unsaturated amide when the reaction aimed at by this invention is performed batchwise or semi-batchwise.

This invention can be implemented batchwise, semi-batchwise, or continuously. When the reaction employed herein is based on a batchwise or semi-batchwise procedure, the supply of the mercapto alkanol and the unsaturated amide may be effected by various methods which are not limited by any particular factor. For example, the mercapto alkanol and the unsaturated amide may be simultaneously placed in the reaction tank and then set reacting, the unsaturated amide may be mixed in advance with a solvent and a catalyst and the mercapto alkanol supplied to the resultant mixture, or the mercapto alkanol may be placed in the reaction tank and subsequently the solution of the unsaturated amide in a solvent supplied to the reaction tank. The unsaturated amide to be used as a raw material herein may be used in its original solid state in the reaction or it may be prepared in the form of an aqueous solution and then put to use.

When a catalyst is used in the reaction, it can be separated from the reaction solution after the completion of the reaction by such a simple procedure as, for example, filtration.

When the reaction is continuously performed by the use of a column adapted to pass the reactants and others therethrough, the separation of the catalyst from the produced reaction solution can be effected by a simple procedure such as, for example, filtration. When the continuous reaction is performed by the use of a packed bed, it obviates the necessity for using an extra procedure for the separation of the catalyst from the reaction solution.

When the product set as a target is a solid substance, the separation and purification thereof from the reaction solution after the completion of the reaction can be attained by crystallization, for example. Depending on the use to which the product is put, the reaction solution having the targeted product dissolved in the solvent may be offered as an industry grade raw material either in its unmodified form or after it has been treated for liberation of the solvent and adjusted to a concentration acceptable for the use.

Now, this invention will be described specifically below with reference to working examples. It should be noted, however, that this invention is not limited in any respect by these examples.

EXAMPLE 1

In a three-neck flask having an inner volume of 100 cc and fitted with a thermometer, a reflux condenser, and a dropping funnel, 7.8 g (0.1 mol) of 2-mercapto ethanol and stirrer chips were placed and stirred by means of a magnetic stirrer and heated to 70° C.

A solution of 7.1 g (0.1 mol) of acrylamide in 20 g of water was placed in the dropping funnel and drip-fed to the content of the flask over a period of about 30 minutes. After the completion of the drip-feeding, the heating and stirring of the content of the flask was continued for three hours. When the reaction solution consequently obtained was analyzed by means of gas chromatography, the conversion of acrylamide was found to be 100%, the selectivity of the targeted amide to be 99%, and the yield to be 99%.

The reaction solution, for the purpose of recrystallization, was distilled under reduced pressure to expel water and induce precipitation of crystals, and then cooled to room temperature, and left standing. As a result, white plate crystals were obtained.

When the produced crystals were tested for various physical properties, they were found to have the structure of 3-[(2-hydroxyethyl)thio]propion amide.

Elementary analysis

|  | C % | H % | N % | O % | S % |
|---|---|---|---|---|---|
| Calculated | 40.25 | 7.43 | 9.39 | 21.45 | 1.49 |
| Found | 40.02 | 7.27 | 9.43 | 22.11 | 21.15 |

Infrared absorption spectrum (KBr tablet method, unit cm$^{-1}$)

(OH stretching vibration) 3395–3199
(Carbonyl stretching vibration) 1648
(Amide N—H stretching vibration) 627
(Amide C—N out-of-plane deformation) 1420
$^1$H NMR spectrum
Determined in bidimethyl sulfoxide solvent based on the TMS standard (see FIG. 1).

EXAMPLE 2

The reaction and analysis were performed by faithfully repeating the procedure of Example 1 while using 20 g of acetone as a solvent in place of water. Consequently, the conversion of acrylamide was found to be 95%, the selectivity of the targeted sulfide (3-[(2-hydroxyethyl)thio] propion amide) to be 98%, and the yield to be 93.

EXAMPLE 3

In an eggplant type flask having an inner volume of 50 cc, 2.28 g (0.02 mol) of maleic acid diamide, 10 cc of water, and 1.57 g (0.02 mol) of 2-mercapto ethanol were placed and, with a reflux condenser attached to the flask, stirred by means of a magnetic stirrer at 80° C. for about three hours to induce a reaction. When the reaction solution consequently obtained was analyzed, the conversion of 2-mercapto ethanol was found to be 99% and the yield of the targeted sulfide (3-[(2-hydroxyethyl)thio]-3-carbamoyl-propion amide) to be 99%.

The reaction solution was distilled under reduced pressure to expel water as the solvent and induce precipitation of a yellow solid product. When this product was dissolved in methanol and the resultant methanol solution was gradually thrown into 100 g of hexane, a white solid substance was obtained.

When the crystals thus obtained were tested for various physical properties, they were found to have the structure of 3-[(2-hydroxyethyl)thio]-3-carbamoyl-propion amide.

Elementary analysis

|  | C % | H % | N % | O % | S % |
|---|---|---|---|---|---|
| Calculated | 37.49 | 6.29 | 14.57 | 29.97 | 16.68 |
| Found | 37.85 | 6.35 | 14.51 | 25.38 | 15.89 |

Infrared absorption spectrum (KBr tablet method, unit cm$^{-1}$)

Figure 2:
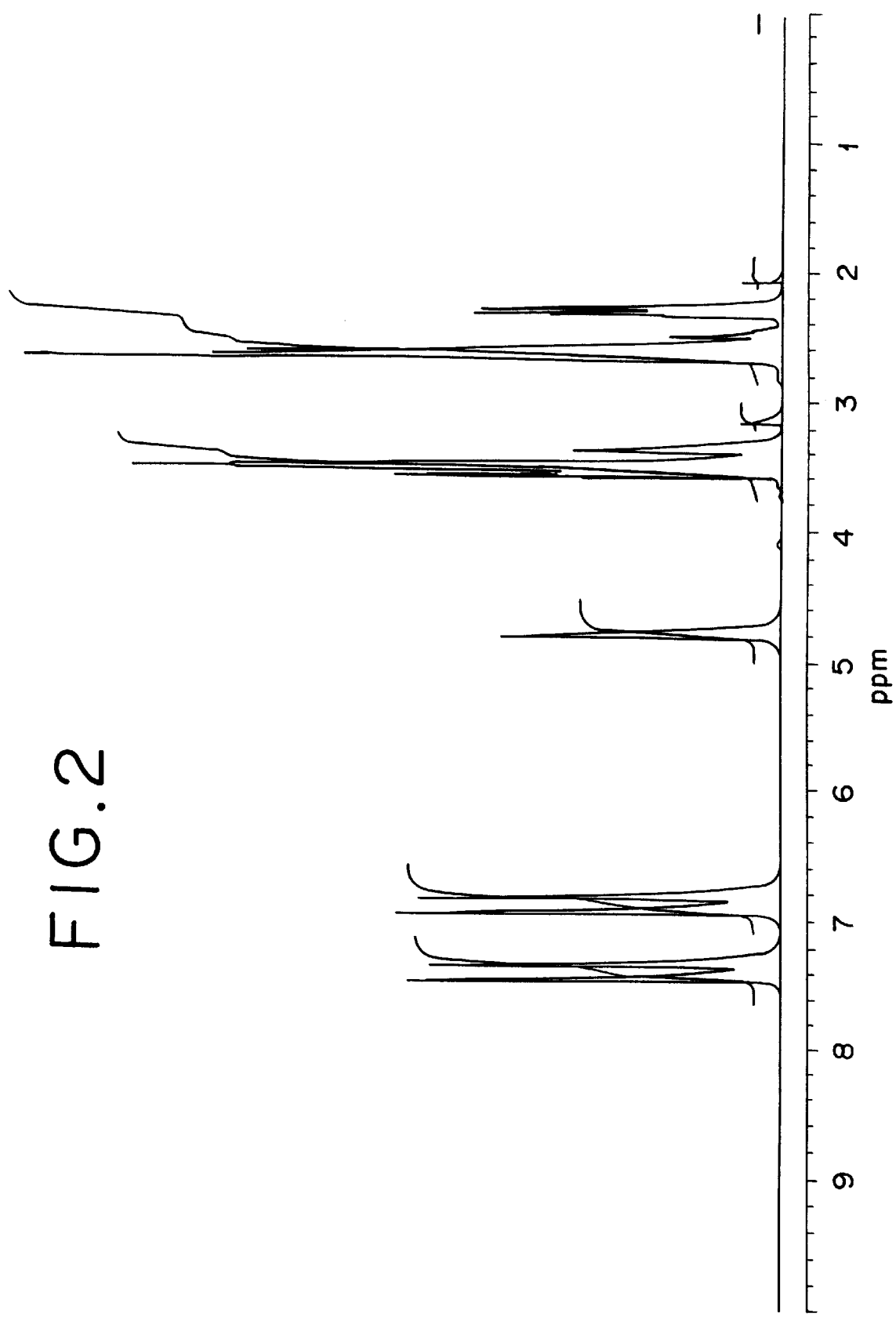
FIG. 2 is a nuclear magnetic resonance spectrum of $^1H$ of the 3-[(2-hydroxyethyl)thio]-3-carbamoyl-propion amide obtained in Example 3 of this invention in bidimethyl sulfoxide solvent according to the TMS standard.

(OH stretching vibration) 3419–3354
(Carbonyl stretching vibration) 1674
(Amide N—H stretching vibration) 650–630
(Amide C—N out-of-plane deformation) 1404
$^1$H NMR spectrum
Determined in bidimethyl sulfoxide solvent based on the TMS standard (see FIG. 2).

EXAMPLE 4

The reaction and analysis were performed by repeating the procedure of Example 3 while using fumaric acid diamide in the place of maleic acid diamide and carrying out the reaction at 100° C. for two hours. As a result, the conversion of fumaric acid diamide was found to be 99% and the yield of the targeted sulfide (3-[(2-hydroxyethyl) thio]-3-carbamoyl-propion amide) to be 98%.

EXAMPLE 5

The reaction and analysis were performed by repeating the procedure of Example 1 while using 1.84 g of 1-methyl-2-mercapto ethanol in place of 2-mercapto ethanol and 1.70 g of methacrylamide in place of acrylamide and carrying out the reaction at 80° C. for six hours. As a result, the conversion of methacrylamide was found to be 93% and the yield of the targeted sulfide (3-[(2-hydroxy-2-methyl-ethyl) thio]-2-methyl-propion amide) to be 92%.

EXAMPLE 6

The reaction and analysis were performed by repeating the procedure of Example 1 while using 6.16 g of 1-phenyl-2-mercapto ethanol in place of 2-mercapto ethanol, 2.54 g of N-butyl-acrylamide in place of acrylamide, and 20 g of ethanol as a solvent in place of water and carrying out the reaction at 60° C. for eight hours. As a result, the conversion of N-butyl-acrylamide was found to be 90% and the yield of the targeted sulfide (3-[(2-hydroxy-2-phenyl-ethyl)thio]-N-butyl-propion amide) to be 89%.

EXAMPLE 7

The reaction and analysis were performed by repeating the procedure of Example 1 while using 2.12 g of 1,2-dimethyl-2-mercapto ethanol in place of 2-mercapto ethanol, 2.56 g of methyl-maleic acid diamide in place of acrylamide, and 0.10 g of an anion-exchange resin (produced by Rohm and Haas Company and marketed under trademark designation of "Amberlite IRA-93") as a catalyst and carrying out the reaction at 60° C. for two hours. As a result, the conversion of methyl-maleic acid diamide was found to be 97% and the yield of the targeted sulfide (3-[(2-hydroxy-1,2-dimethyl-ethyl)thio]-3-carbamoyl-2-methyl-propion amide) to be 96%.

What is claimed is:

1. A method for the production of an organic sulfide compound of the formula (I):

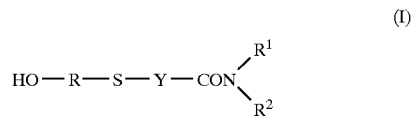

wherein R represents a hydrocarbon residue of 2 to 8 carbon atoms, R$^1$ and R$^2$ independently represent a hydrogen atom or a hydrocarbon residue of 1 to 4 carbon atoms, and Y represents a group of the formula (II):

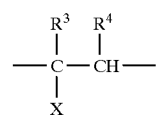

or of the formula (III):

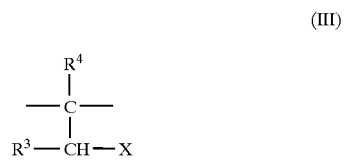

wherein R$^3$ and R$^4$ independently represent a hydrogen atom, methyl or ethyl and X represents a hydrogen atom or

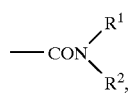

comprising reacting in water a mercapto alkanol of the formula (IV):

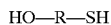   (IV)

with an unsaturated amide of the formula (V):

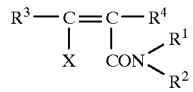   (V)

2. A method according to claim 1, wherein the amount of said mercapto alkanol to be used is in the range of 0.5 to 3 mols per mol of said unsaturated amide.

3. A method according to claim 1, wherein said reaction is carried out at a temperature in the range of 20° to 150° C.

4. A method according to claim 1, wherein said reaction is carried out in the presence of a solid basic catalyst.

5. A method according to claim 4, wherein said catalyst is an anion-exchange resin.

6. A method according to claim 4, wherein the amount of said catalyst to be used is in the range of 0.5 to 40% by weight based on the amount of the unsaturated amide.

* * * * *